US010376215B2

(12) United States Patent
Zhou (10) Patent No.: US 10,376,215 B2
(45) Date of Patent: Aug. 13, 2019

(54) SMART TOILET WITH A FUNCTION OF HUMAN BLOOD PRESSURE DETECTION (71) Applicant: Zhongshan Anbo Health Technology Co., Ltd., Zhongshan (CN)

(72) Inventor: Wenhui Zhou, Zhongshan (CN)

(73) Assignee: ZHONGSHAN MEITU PLASTIC INDUSTRY CO., LTD., Zhongshan (CN)

( * ) Notice: Subject to any disclaimer, the term of this patent is extended or adjusted under 35 U.S.C. 154(b) by 0 days.

(21) Appl. No.: 15/915,077

(22) Filed: Mar. 8, 2018

(65) Prior Publication Data

US 2018/0271447 A1 Sep. 27, 2018

(30) Foreign Application Priority Data

Mar. 24, 2017 (CN) .......................... 2017 1 0182438

(51) Int. Cl.
*A47K 17/02* (2006.01)
*E03D 9/08* (2006.01)
*A61B 5/00* (2006.01)
*A47K 10/48* (2006.01)
*A47K 13/30* (2006.01)
*A61B 5/022* (2006.01)

(52) U.S. Cl.
CPC ............ *A61B 5/6891* (2013.01); *A47K 10/48* (2013.01); *A47K 13/305* (2013.01); *A47K 17/026* (2013.01); *A61B 5/02233* (2013.01); *A61B 5/742* (2013.01); *A61B 5/7475* (2013.01); *E03D 9/08* (2013.01); *A61B 5/741* (2013.01); *A61B 2560/029* (2013.01); *A61B 2560/0425* (2013.01)

(58) Field of Classification Search
CPC ... A61B 5/6891; A61B 5/02233; A61B 5/742; A61B 5/741; A61B 5/7475; A47K 10/48; A47K 13/305; A47K 17/026; E03D 9/08
USPC .................................................. 4/420.4, 661
See application file for complete search history.

(56) References Cited

U.S. PATENT DOCUMENTS

| 5,111,539 A * | 5/1992 | Hiruta ................. A61B 5/02241 4/301 |
| 5,735,798 A * | 4/1998 | Shinohara .............. A61B 5/022 4/314 |
| 9,595,185 B1* | 3/2017 | Hall .......................... E03D 5/10 |
| 2018/0078191 A1* | 3/2018 | Hall ........................ G16H 50/30 |
| 2018/0084959 A1* | 3/2018 | Hall ........................ A47K 13/24 |

* cited by examiner

Primary Examiner — Huyen D Le
(74) Attorney, Agent, or Firm — Gokalp Bayramoglu (57) ABSTRACT A smart toilet with a function of human blood pressure detection, the smart toilet includes a toilet base. The smart toilet further includes a body connected to the toilet base. The body is provided with a controller and a human blood pressure detection module, a display or voice prompt module, a key input module for sending back operation information of the user to the controller, and a power supply module for supplying power, which are electrically connected to the controller respectively. The controller processes the electrical signal transmitted by the human blood pressure detection module to obtain the blood pressure value of the human body, and controls the display or voice prompt module to output the blood pressure value. The human blood pressure can be conveniently and rapidly detected while the users use the toilet every day, so that abnormal blood pressure can be discovered early.

26 Claims, 6 Drawing Sheets

SMART TOILET WITH A FUNCTION OF HUMAN BLOOD PRESSURE DETECTION

CROSS REFERENCE TO RELATED APPLICATIONS

This application is based upon and claims priority to Chinese Patent Application No. CN201710182438.X, filed on Mar. 24, 2017, the entire content of which is incorporated herein by reference.

TECHNICAL FIELD

The present invention relates to a toilet, particularly to a smart toilet with a function of human blood pressure detection.

BACKGROUND OF THE INVENTION

The main functions which existing smart toilets provide are heating-up of the toilet bases, cleaning with warm water, drying with warm air, and deodorization. However, overall, functions are limited, and the usage is invariant. It is hard to make a breakthrough. In recent years, with the increasing requirements of people for the quality of life, the demand for health standards is getting higher and higher. It is a trend that the personal health care functions can be introduced into the smart toilet. However, some existing smart toilets cannot satisfy the requirements of people to understand their health conditions. At the same time, with the increase of people's living standards, the diet has undergone big changes, and the number of people suffering from hypertension is also on the rise, so hypertension has become a matter of concern. In addition, it is not convenient to measure the blood pressure with the existing blood pressure measurement devices. Even if the user develops a blood pressure measurement monitoring plan, he may forget to follow the plan because of busy work schedule, or he may not perform the measurement due to misplacement of the blood pressure measurement device. Therefore, how to make people conveniently and regularly measure blood pressure has become an important issue.

SUMMARY OF THE INVENTION

In order to solve the deficiencies of the prior art, the present invention provides n smart toilet with a function of human blood pressure detection, and the human blood pressure can be conveniently and quickly detected when users use toilet every day, so that abnormal blood pressure can be discovered early.

The technical solutions adopted by the present invention are shown as below:

A smart toilet with a function of human blood pressure detection, the smart toilet comprising toilet base 2. The smart toilet further comprises body 1 connected to the toilet base. Body 1 is provided with controller 3 and human blood pressure detection module 4, display or voice prompt module 5, key input module 6 configured for sending operation information of the user back to controller 3, and power supply module 30 for supplying power, which are electrically connected to controller 3 respectively. Human blood pressure detection module 4 comprises detection airbag 42 which is a closed or a non-closed ring after being inflated when the blood pressure is detected, pressure sensor 41 provided on detection airbag 42, air pump 44 configured for inflating detection airbag 42 and solenoid valve or proportional valve or exhaust valve 43 for deflating detection airbag 42. Air pump 44 and solenoid valve or proportional valve or exhaust valve 43 are electrically connected to controller 3 respectively. Human blood pressure detection module 4 further comprises airbag clamp 45 provided on the body, configured to clamp the inflated detection airbag 42 in the finger, wrist, or arm of the human body. Controller 3 is used to control the air pump or solenoid valve or proportional valve or exhaust valve 43 to inflate or deflate the detection airbag 42. Controller 3 processes the electrical signal transmitted by the pressure sensor to obtain a blood pressure value of the human body and controls display or voice prompt module 5 to output the blood pressure value.

Body 1 comprises main body 10 and toilet seat 12 pivotally connected to the main body 10, wherein after being rotated, toilet seat 12 covers toilet base 2.

Body 1 includes main body 10 and armrest 11 provided on main body 10. Airbag clamp 45 is finger hole 111 configured on armrest 11 for inserting the finger. Detection airbag 42 is provided inside finger hole 111.

Airbag clamp 45 includes supporting portion 450 provided on body 1 and clamping portion 451 provided on supporting portion 450. The supporting portion, the clamping portion or the supporting portion and the clamping portion is/are provided with or formed with detection ring 453 for accommodating a human finger or a wrist or an arm. Detection ring 453 is provided with detection inlet 454 for allowing or restricting a human finger or a wrist or an arm to enter into or leave from detection ring 453. Detection airbag 42 is provided on detection ring 453. The airbag clamp further includes driving device 452, wherein driving device 452 is electrically connected to the controller, and drives clamping portion 451 to move relative to supporting portion 450, such that detection inlet 454 is expanded or narrowed to allow the human finger or the wrist or the arm to enter into or leave from detection ring 453.

Airbag clamp 45 comprises the supporting portion arranged on the body, a clamping portion arranged on the supporting portion, a driving device electrically connected to the controller; wherein the driving device drives the clamping portion to move relative to the supporting portion, such that the clamping portion or the supporting portion and the clamping portion forms/form a closed or non-closed ring, which surrounds the human finger or the wrist or the arm. The detection airbag is provided on the clamping portion and/or the supporting portion.

The body comprises main body 10 and armrest 11 provided on main body 10. Supporting portion 450 on airbag clamp 45 is provided on armrest 11.

Clamping portion 451 comprises first clamping portion 4511 and second clamping portion 4512; free ends 4513 and driving ends 4514 are respectively provided on first clamping portion 4511 and second clamping portion 4512. Driving ends 4514 of first clamping portion 4511 and second clamping portion 4512 are connected to driving device 452. Free ends 4513 of first clamping portion 4511 and second clamping portion 4512 move close or away from each other when first clamping portion 4511 and second clamping portion 4512 are driven by driving device 452 to move relative to the supporting portion, so that detection inlet 454 is expanded or narrowed.

Detection airbag 42 includes airbag body 420 and connecting ends 421 located at two ends of airbag body 420, wherein connecting ends 421 are connected to free ends 4513 of first clamping portion 4511 and second clamping portion 4512.

The first clamping portion 4511 and second clamping portion 4512 are arc-shaped. Supporting portion 450 includes supporting portion body 4500; wherein supporting portion body 4500 is U-shaped and works as detection ring 453.

Free end 4513 of first clamping portion 4511 is provided with a protrusion, and free end 4513 of second clamping portion 4512 is provided with a groove fitted with the protrusion provided on free end 4513 of first clamping portion 4511.

Sliding grooves 4501 are provided on supporting portion 450, and first clamping portion 4511 and second clamping portion 4512 are each provided with sliding portion 4515 for engaging with sliding grooves 4501. Driving device 452 includes first driving rod 4521 and second driving rod 4522 respectively hinged with driving ends 4514 of first clamping portion 4511 and second clamping portion 4512, movable driving block 4523 hinged with the other ends of first driving rod 4521 and second driving rod 4522, driving airbag 4524 provided between movable driving block 4523 and supporting portion 450 to push movable driving block 4523 to move, an air pump electrically connected to the controller and used for inflating driving airbag 4524, a solenoid valve or a proportional valve or an exhaust valve electrically connected to the controller for deflating driving airbag 4524, a reset spring provided between supporting portion 450 and movable driving block 4523 to push movable driving block 4523 to reset. The movable driving block is located between the driving airbag and the reset spring.

Airbag clamp 45 further comprises a hand sensing module electrically connected to the controller, wherein the hand sensing module is used to detect whether the human finger, the wrist, or the arm is located in detection ring 453 or on supporting portion 450.

The hand sensing module comprises a capacitive sensor or a pressure sensor, a light touch switch, a sensing electrode plate, a button switch, or an infrared sensor provided on supporting portion 450 or clamping portion 451 or detection airbag 42. The capacitive sensor, the pressure sensor, the light touch switch, or the sensing electrode plate or the button switch or the infrared sensor are electrically connected to controller 3.

The smart toilet further comprises human body sensing module 7 electrically connected to controller 3 and used for detecting whether the human body has sat down.

Human body sensing module 7 comprises a capacitive sensor, a pressure sensor, or a sensing electrode plate. The capacitive sensor, the pressure sensor, or the sensing electrode plate is electrically connected to controller 3 and used for detecting whether the human body has sat down. The capacitive sensor, the pressure sensor, or the sensing electrode plate is provided on toilet base 2 or the body 1.

The smart toilet further comprises toilet seat temperature controlling module 8 electrically connected to controller 3 and used for controlling the temperature of the toilet seat. The toilet seat temperature controlling module 8 comprises a temperature sensor and a toilet seat heating module which are respectively arranged on the toilet seat and are respectively electrically connected to the controller.

The smart toilet further comprises user cleaning module 9 electrically connected to controller 3, and user cleaning module 9 includes water spraying module 90 for providing cleaning water, water pressure control module 91 for controlling the water pressure of the cleaning water, water temperature control module 92 for controlling the water temperature of the cleaning water, fan module 94 for providing drying air and air temperature control module 93 for controlling the temperature of the drying air; wherein water pressure control module 91, water temperature control module 92, air temperature control module 93, are electrically connected to the controller.

Water spraying module 90 comprises a water outlet nozzle, a water pipe connected to the water outlet nozzle and the external water source. Water temperature control module 92 comprises a temperature sensor and a cleaning water heating module which are respectively arranged on the water pipe and electrically connected to controller 3. Water pressure control module 91 comprises a proportional valve provided between the water outlet nozzle and the water pipe and is electrically connected to the controller. Air temperature control module comprises a temperature sensor and a drying air heating module respectively electrically connected to the controller.

The smart toilet further comprises communication module 31 electrically connected to the controller. Communication module 31 communicates with the smart device. The human blood pressure is transmitted to the smart device and displayed on the smart device by the communication module.

A method for controlling a smart toilet with human blood pressure detecting function, comprising the following steps:

A: Power-on Initialization: Initializing an initial state of each connection module through controller 3;

B: Performing self-checking: Performing fault detection on each module through controller 3; if self-checking is passed, proceeding to step C; otherwise, conducting an exception handling, displaying or reporting exception information through a display or voice prompt module 5;

C: Entering into a main cycle, detecting whether a person has sat down by controller 3 through human body sensing module 7. If the person has sat down, starting human blood pressure detection module 4 by controller 3 and proceeding to step D; if no one has sat down, controlling human blood pressure detection module 4 to enter dormancy by controller 3 and proceeding to step D.

D: Detecting whether there is an input at key input module 6 by controller 3, if there is no input, returning to step C; if there is an input, proceeding to step E;

E: Performing corresponding operations according to the input of key input module 6 by controller 3: setting the temperature of the cleaning water, the water pressure of the cleaning water, the temperature of the drying air, and starting user cleaning module 9 to provide cleaning water or drying air;

The smart toilet comprises toilet base 2, and further comprises body 1 connected to the toilet base. Body 1 is provided with controller 3 and human blood pressure detection module 4, display or voice prompt module 5, key input module 6 configured for sending operation information of the user back to controller 3, and power supply module 30 for supplying power, which are electrically connected to the controller respectively. Human blood pressure detection module 4 comprises detection airbag 42 which is closed or non-closed ring after being inflated when detecting the blood pressure, pressure sensor 41 provided on detection airbag 42 and electrically connected to the controller, air pump 44 configured for inflating detection airbag 42 and solenoid valve or proportional valve or exhaust valve 43 for deflating detection airbag 42, wherein air pump 44 and solenoid valve or proportional valve or exhaust valve 43 are electrically connected to controller 3. Human blood pressure detection module 4 further comprises airbag clamp 45 configured to clamp an inflated detection airbag 42 on a finger, wrist, or arm of the human body. Controller 3 is used to control air pump 44 or solenoid valve or proportional valve or exhaust valve 43 to inflate or deflate detection airbag 42, and controller 3 processes the electrical signal transmitted by the pressure sensor to obtain the blood pressure value of the human body and controls display or voice prompt module 5 to output the blood pressure value.

The smart toilet further comprises human body sensing module 7 electrically connected to controller 3 and used for sensing whether the human body has sat down.

The smart toilet further comprises user cleaning module 9 electrically connected to controller 3, and user cleaning module 9 includes water spraying module 90 for providing cleaning water, water pressure control module 91 for controlling the water pressure of the cleaning water, water temperature control module 92 for controlling the temperature of the cleaning water, fan module 94 for providing drying air and air temperature control module 93 for controlling the temperature of the drying air. Water pressure control module 91, water temperature control module 92, air temperature control module 93 are electrically connected to the controller.

Body 1 comprises main body 10 and toilet seat 12 pivotally connected to main body, wherein after being rotated, toilet seat 12 covers toilet base 2. The smart toilet further comprises toilet seat temperature controlling module 8 electrically connected to controller 3 for controlling the temperature of the toilet seat, wherein toilet seat temperature controlling module 8 comprises a temperature sensor and a toilet seat heating module which are respectively arranged on the toilet seat and are respectively electrically connected to the controller. The step E further comprises performing corresponding operations according to the input of key input module 6: setting the temperature of the toilet seat, and starting the toilet seat temperature controlling module to adjust the temperature of the toilet seat.

The step E further comprises performing corresponding operations according to the input of key input module 6: starting human blood pressure detection module 4 by controller 3, the electrical signal related to the human blood pressure is obtained by the pressure sensor and is transmitted to the controller. Controller 3 processes the obtained electrical signal to obtain the blood pressure value of the human body and controls the display or voice prompt module or communicate module 31 which communicates with the smart device to output the blood pressure value.

Human body sensing module 7 comprises a capacitive sensor or a pressure sensor or a sensing electrode plate, wherein the capacitive sensor or the pressure sensor or the sensing electrode plate is electrically connected to controller 3 for detecting whether the human body has sat down, and the capacitive sensor or the pressure sensor or the sensing electrode plate is provided on toilet base 2 or body 1.

Compared with the prior arts, the advantages of the present invention are shown as below:

1. A smart toilet with a human blood pressure detection function, wherein the smart toilet comprises a toilet base. The smart toilet further comprises a body connected to the toilet base. The smart toilet further comprises a controller and a human blood pressure detection module, a display or voice prompt module, a key input module configured for sending operation information of the user back to the controller, and a power supply module for supplying power. The human blood pressure detection module, the display or voice prompt module, the key input module and the power supply module are electrically connected to the controller respectively. The human blood pressure detection module obtains electrical signals associated with the blood pressure of the human body and transmits the electrical signals to the controller. The controller processes the obtained electrical signals to obtain the blood pressure value and outputs the data through the display or the voice prompt module. The present invention is convenient for the user to know his/her own blood pressure status while using the toilet every day, and this blood pressure measurement has the advantages of being convenient and fast.

2. The core of the present invention for measuring blood pressure is a human blood pressure detection module. The human blood pressure detection module comprises a detection airbag, a pressure sensor arranged on the detection airbag, an air pump, and a solenoid valve, a proportional valve, or an exhaust valve, an airbag clamp configured to press the inflated detection airbag against the finger, wrist, or arm of the human body. The controller controls the air pump or the solenoid valve, the proportional valve, or the exhaust valve to make the detection airbag inflate or deflate. The controller processes the electrical signals transmitted by the pressure sensor to obtain a human blood pressure value and controls the display or voice prompt module to output the blood pressure value. The human blood pressure detection module of the present invention has advantages of simple structure and easy implementation.

3. As a further improvement of the present invention, the airbag clamp for clamping an inflated detection airbag to a finger, a wrist or an arm of a human body comprises: a supporting portion, a clamping portion, and a driving device, wherein the supporting portion or the clamping portion or the supporting portion and the clamping portion are provided with or formed with a detection ring for accommodating a finger or a wrist or an arm of a human. The detection ring is provided with a detection inlet that allows or restricts human's finger or wrist or arm to enter or leave the detection ring. The detection airbag is provided on the detection ring. When the user measures the blood pressure, first, the finger or the wrist or the arm is placed on the detection ring through the detection inlet. The controller controls the driving device to drive the clamping portion to move relative to the supporting portion according to an operation at the key input module or a sensing state of additionally provided hand sensing module, to make the detection inlet narrow or directly closed, so that the human finger or wrist or arm is enclosed in the detection ring. Then the controller activates the human blood pressure detection module to measure the blood pressure. After detecting the blood pressure, the controller controls the driving device to expand the detection inlet, so that the user can remove the finger or wrist or arm. The setting of the airbag clamp allows the user to get rid of the cumbersome operation of wrapping the airbag on the hand required by the traditional blood pressure measurement, which makes blood pressure detection more convenient; meanwhile, the airbag clamp is provided with a detection ring, which makes it easy for users to place their fingers, wrists, or arms.

DETAILED DESCRIPTION OF THE INVENTION

The embodiments of the present invention will be further described in detail with reference to the accompanying drawings.

Figure 5:
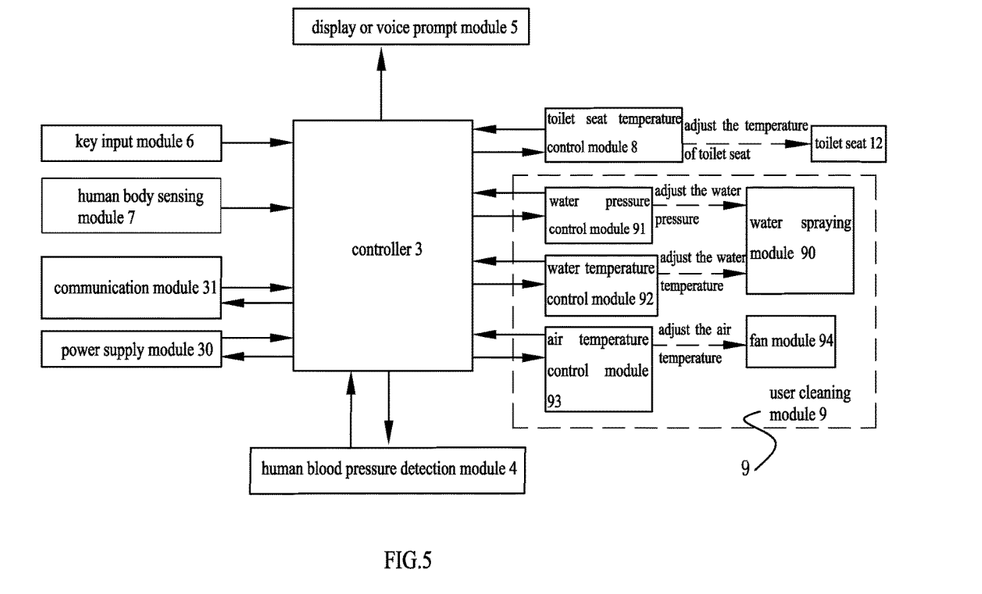
FIG. 5 is a system block diagram of the present invention.
Figure 6:
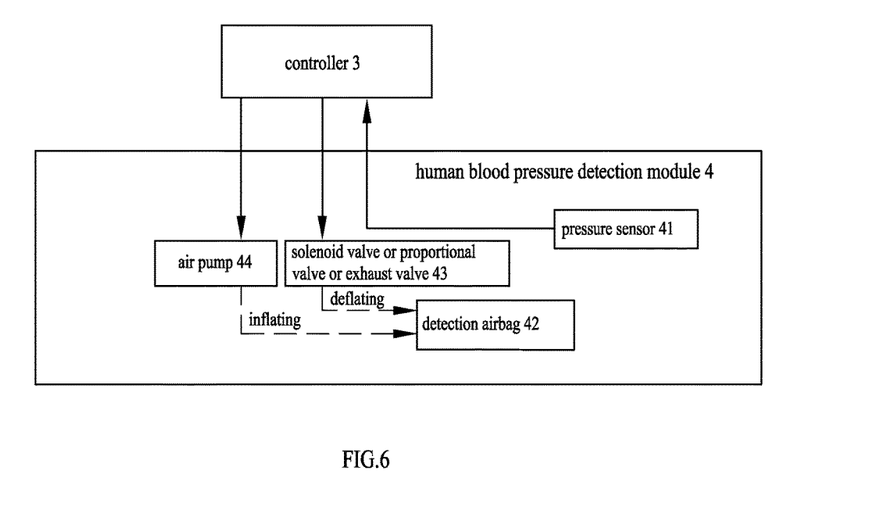
FIG. 6 is a block diagram of a human blood pressure detection module of the present invention.

A smart toilet with a function of human blood pressure detection, the smart toilet comprises toilet base 2, characterized in that the smart toilet further comprises body 1 connected to the toilet base. Body 1 is provided with controller 3, and human blood pressure detection module 4, display or voice prompt module 5, key input module 6 configured for sending operation information of the user back to controller 3, and power supply module 30 for supplying power. Human blood pressure detection module 4, display or voice prompt module 5, key input module 6, and power supply module 30 are electrically connected to the controller respectively. Human blood pressure detection module 4 comprises inflated detection airbag 42 which is closed or non-closed ring shape when detecting the blood pressure, pressure sensor 41 provided on detection airbag 42 and electrically connected to the controller, air pump 44 configured for inflating detection airbag 42 and solenoid valve or proportional valve or exhaust valve 43 for deflating detection airbag 42, wherein air pump 44 and solenoid valve or proportional valve or exhaust valve 43 are electrically connected to controller 3 respectively. Human blood pressure detection module 4 further comprises airbag clamp 45 arranged on the body and configured to clamp the inflated detection airbag 42 on the finger, wrist, or arm of the human body. Controller 3 is used to control the air pump and solenoid valve or proportional valve or exhaust valve 43 to inflate or deflate detection airbag 42. Controller 3 processes electrical signals transmitted by the pressure sensor to obtain the blood pressure value of the human body and controls display or voice prompt module 5 to output the blood pressure value. The electrical signals are referred to as current or voltage signals.

The method for measuring the blood pressure of a human body according to the present invention is an oscillometric method, also called oscillating method. Firstly, a finger, a wrist, or an arm is placed in a detection airbag. When detecting the blood pressure, the inflated airbag is tightly attached to the finger, wrist, or arm of the human body by the airbag clamp. The key input module or the hand sensing module for sensing whether the human finger, the wrist, or the arm is at the detection position is used to inform the controller to start the blood pressure detection. The controller controls the air pump to inflate the detection airbag until the pressure of the detection airbag applied to the finger, wrist or arm is enough to stop the arterial blood flow, and then the controller controls the solenoid valve or the proportional valve or the exhaust valve to deflate the detection airbag. When deflation is in a certain degree, the blood can flow through the blood vessels and have certain oscillation waves. With gradually deflation, the oscillation waves get bigger and bigger. In the deflation process, due to the contact between the detection airbag and the finger or wrist or arm is no longer tight, oscillation waves are smaller and smaller. Oscillation waves are transmitted by the detection airbag to the pressure sensor, and the pressure sensor can detect the pressure and pressure fluctuations of the detection airbag.

The pressure sensor will send all the detected pressure signals to the controller. The detected pressure signals are filtered, amplified, analog-to-digital converted to obtain the oscillation wave data by the controller. The method for searching systolic blood pressure and diastolic blood pressure based on the oscillatory wave data is as follows. In the oscillatory wave data, the time of the largest fluctuation is selected as the reference point. On the basis of the reference point, a fluctuation point of 0.45 times the peak is searched forward, and this fluctuation point corresponds to the pressure of systolic blood pressure; a fluctuation point of 0.75 times the peak is searched backward, and this fluctuation point corresponds to the pressure of diastolic blood pressure. It should be noted that the constants of 0.45 and 0.75 vary from person to person and should be set based on the results of clinical tests. Moreover, different blood pressures may be segmented and set with different constants accordingly. The controller obtains the human blood pressure value according to the method for searching systolic blood pressure and diastolic blood pressure and the obtained oscillation wave data, and the obtained blood pressure value of the human body will be output through display or voice prompt module 5.

Embodiment 1

Figure 1:
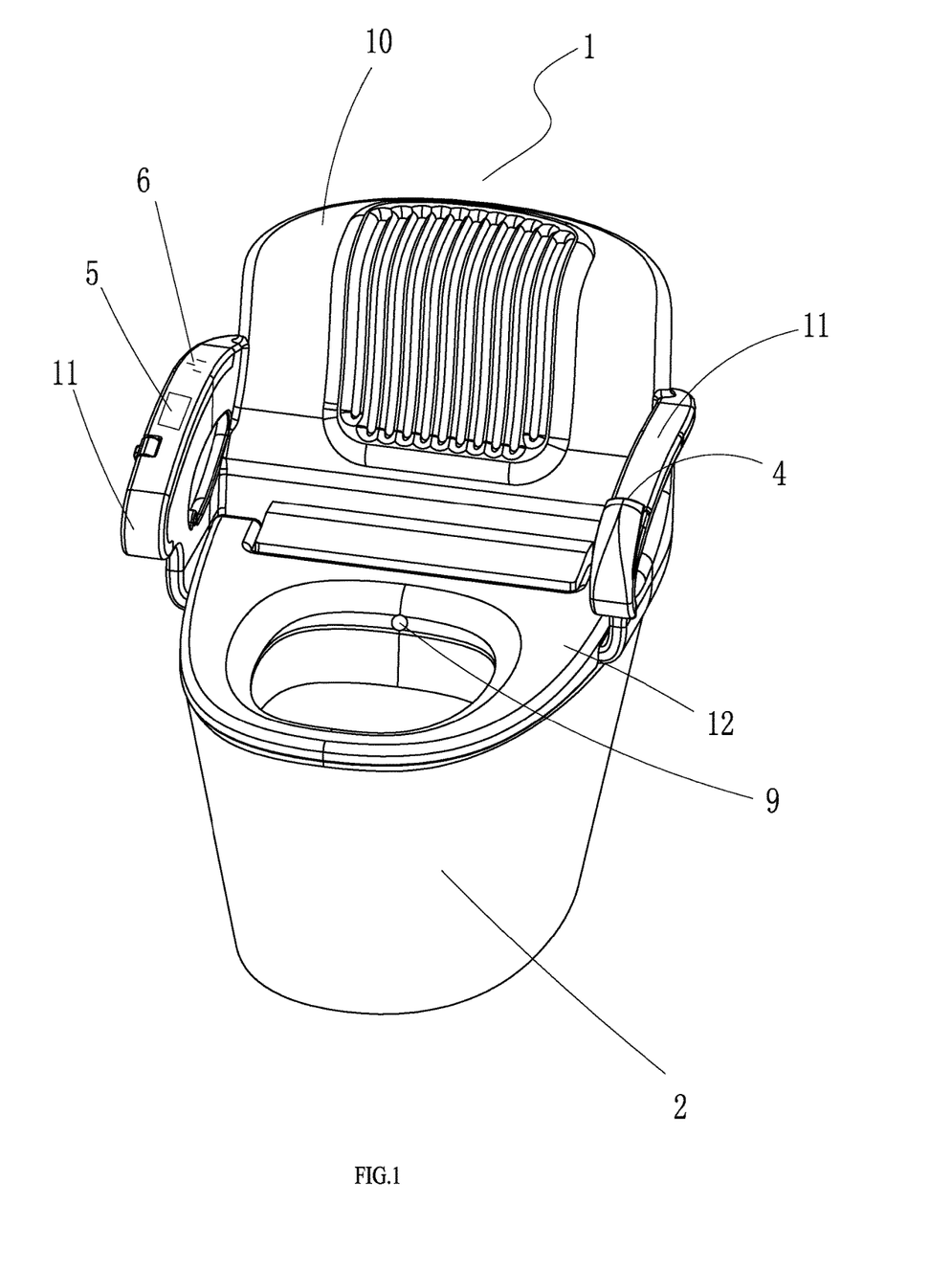
FIG. 1 is a schematic perspective view of Embodiment 1 of the present invention.
Figure 2:
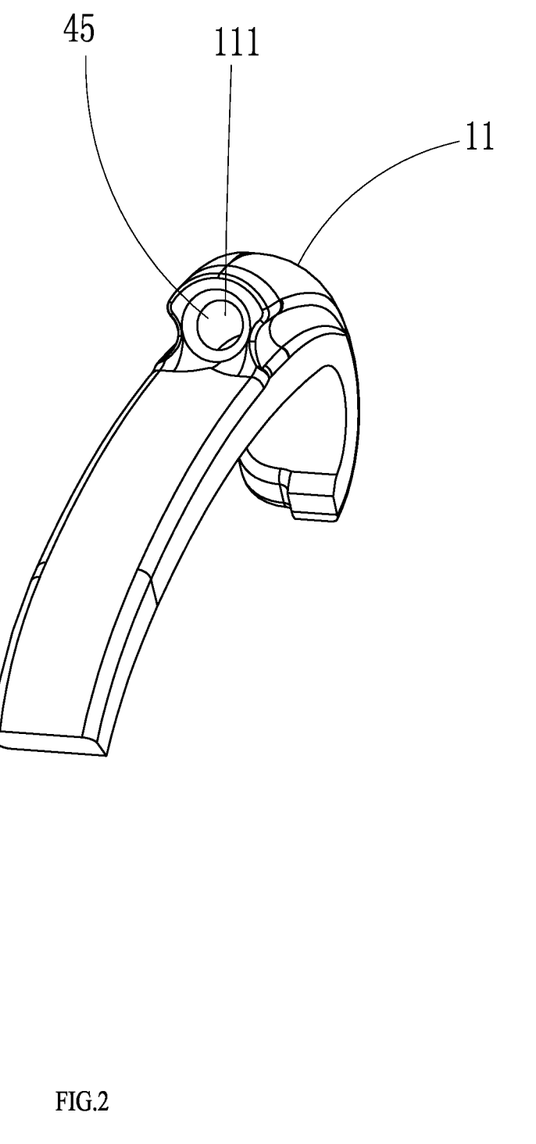
FIG. 2 is a schematic view of an armrest structure of Embodiment 1 of the present invention.

Referring to FIG. 1 to FIG. 2, body 1 includes main body 10 and armrest 11 provided on main body 10. Airbag clamp 45 is finger hole 111 provided on armrest 11 for inserting the finger. Detection airbag 42 is provided inside finger hole 111. The airbag clamp in the Embodiment 1 is the finger hole provided on the armrest, and the detection airbag and the pressure sensor on the detection airbag are arranged inside the finger hole. The preferred method of finger-type blood pressure detection method is adopted here. When the user performs blood pressure measurement, the finger is placed in the finger hole. The key input module is operated, and the controller controls the inflation or deflation of the detection airbag, so that the pressure sensor on the detection airbag obtains electrical signals of relevant data and transmits the electrical signals to the controller. The controller calculates the blood pressure value of the human body according to the oscillometric method of the blood pressure detection described above and outputs the data through the display or the voice prompt module. With the embodiment of the present invention having the above structure, since the finger-type blood pressure detection method is adopted, the airbag clamp has a small volume and the user can easily operate the detection of the blood pressure.

Embodiment 2

Figure 3:
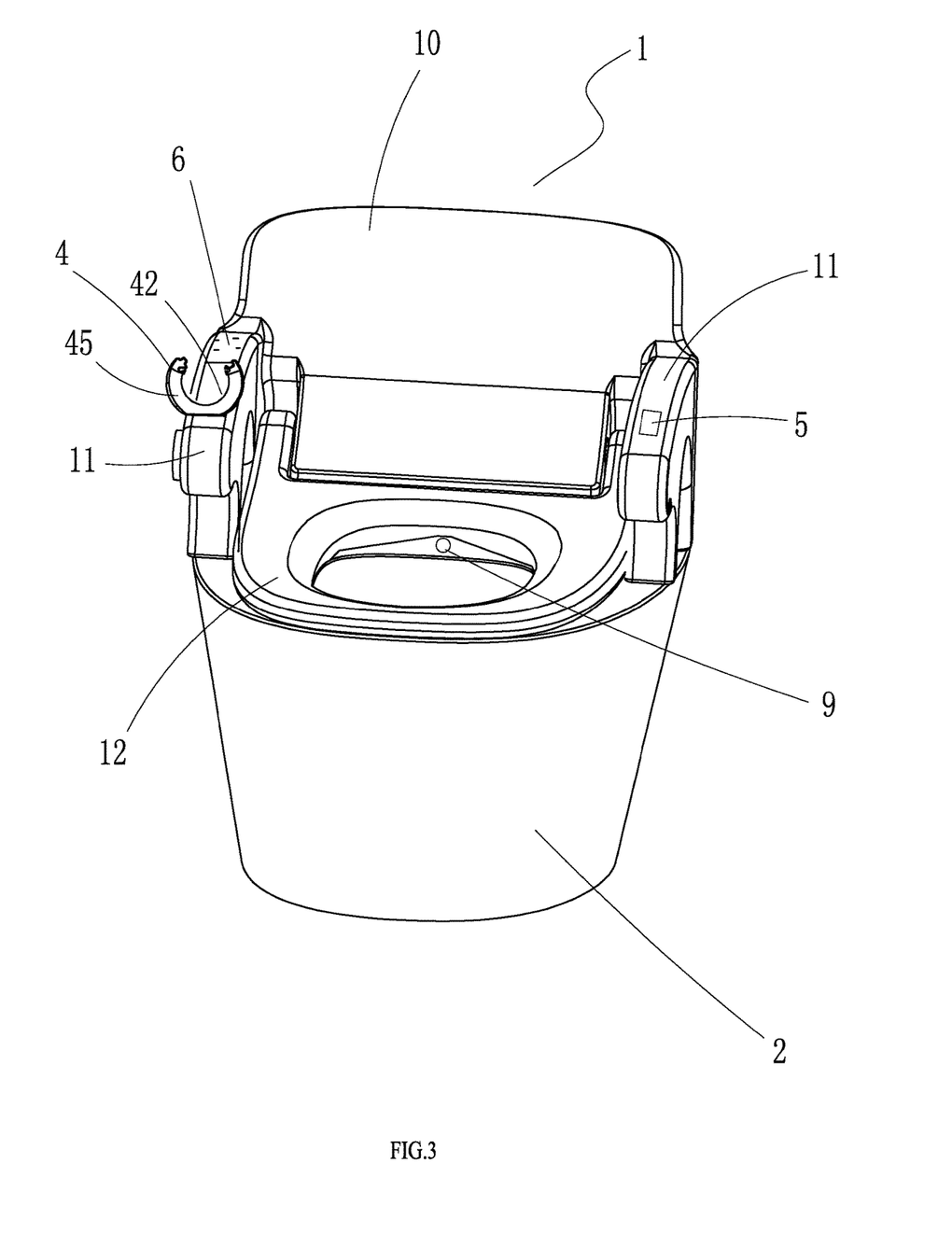
FIG. 3 is a perspective view of Embodiment 2 of the present invention.
Figure 4:
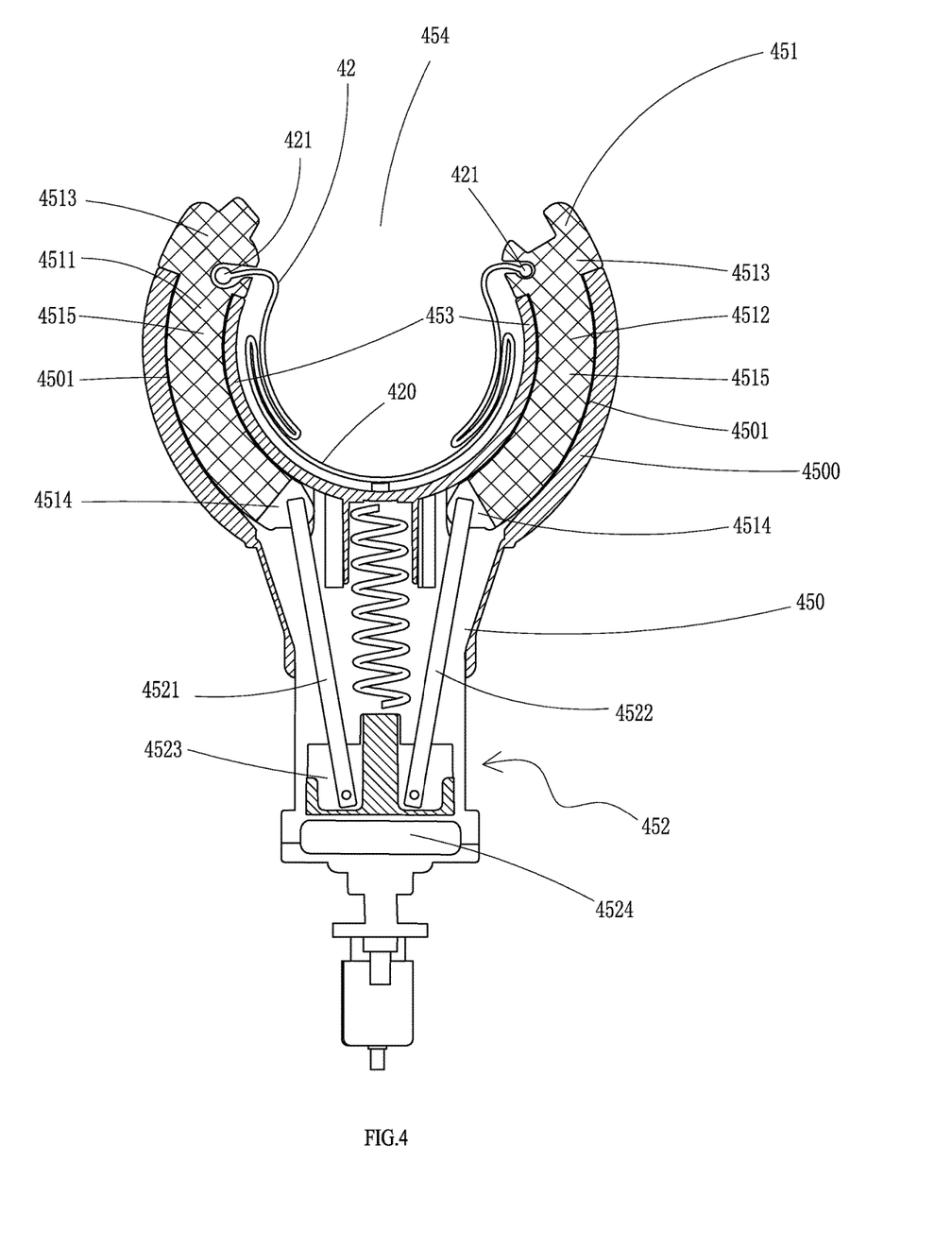
FIG. 4 is a longitudinal sectional view of the present invention after the airbag clamp of Embodiment 2 of the present invention has been removed.

FIG. 3 to FIG. 4 show embodiment 2.

Airbag clamp 45 includes supporting portion 450 provided on body 1 and clamping portion 451 provided on support portion 450, wherein the supporting portion, the clamping portion, or the supporting portion and the clamping portion is provided with or formed with detection ring 453 for accommodating a human finger or a wrist or an arm. Detection ring 453 is provided with detection inlet 454 for allowing or restricting the human finger or the wrist or the arm to enter into or leave from detection ring 453. Detection airbag 42 is provided on detection ring 453. The airbag clamp further includes driving device 452, wherein driving device 452 is electrically connected to the controller, and drives clamping portion 451 to move relative to supporting portion 450, such that detection inlet 454 expands or contracts to allow the human finger or the wrist or the arm to enter into or leave from detection ring 453. The detection ring can be provided on the supporting portion, and the shape of the supporting portion forms the detection ring. The detection ring can also be provided on the clamping portion, and the shape of the clamping portion forms the detection ring. Further, the detection ring can be formed by the supporting portion and clamping portion together. The finger, wrist, or arm of the human body entering into the detection ring means that the finger, wrist or arm of the human body enters into the detection ring, and is surrounded by the detection ring.

When the blood pressure detection is performed, first, the user places a finger, wrist, or arm into the detection ring. According to the user's operation at the key input module or the information signal from the additionally provided hand sensing module, the controller controls the driving device to drive the clamping portion to move relative to the supporting portion, so that the detection inlet on the detection ring is closed or narrowed, whereby the detection ring encloses the human finger, wrist, or arm and restrains the finger, wrist, or arm of the human body from leaving the detection ring from the detection inlet. Meanwhile, the detection airbag is located between the human finger or wrist or arm and the detection ring. When the detection airbag is inflated, the detection airbag is tightly compressed between the detection ring and the human finger or wrist or arm, and the pressure sensor on the detection airbag is thus close to the blood vessels of the human body, obtaining the accurate data. After the above steps are completed, the controller can start the human blood pressure detection module to detect the blood pressure of the human body. The detection inlet is preferably closed during blood pressure detection, so that the entire detection ring forms a complete ring with better strength when blood pressure is measured. However, if the clamping portion and the supporting portion have sufficient strength and rigidity, the detection inlet is also allowed to be opened and just be narrowed to the degree that the finger, the wrist, or the arm of the human body cannot be easily removed from the detection ring when the blood pressure detection is performed.

Of course, the following preferable design may also be made: Airbag clamp 45 includes a supporting portion provided on the body, a clamping portion provided on the supporting portion, and a driving device electrically connected to the controller, wherein the driving device drives the clamping portion to move relative to the supporting portion, such that the clamping portion or the supporting portion and the clamping portion forms a closed or open ring surrounding the finger, wrist or arm of the human body. The detection airbag is provided on the clamping portion and/or the supporting portion. The airbag clamp can be provided without a fixed detection ring. When the user detects the blood pressure, first, the finger or the wrist or the arm is placed on the supporting portion, and the controller controls the driving device to drive the clamping portion to move relative to the supporting portion, such that the clamping portion or the supporting portion and the clamping portion forms/form a closed or opened ring surrounding the human finger or wrist or arm. The closed or opened ring is equivalent to the detection ring, and is formed when detecting the blood pressure, instead of being set at the beginning. The detection airbag is already located between the human finger, the wrist, or the arm and the airbag clamp when detecting the blood pressure, and when the detection airbag is inflated, the detection airbag is tightly compressed between the detection ring and the human finger or wrist or arm. Finally, the controller starts the human blood pressure detection module for blood pressure detection. After the blood pressure measurement is completed, the controller controls the driving device to drive the clamping portion to move relative to the supporting portion so that the position of the clamping portion is reset, and the user can remove the finger, the wrist, or the arm. This design is beneficial to hide the airbag clamp, making the appearance of the present invention more harmonious. Further, in the preferred embodiment, a hand sensing module electrically connected to the controller for sensing whether the human finger, the wrist, or the arm is on the supporting portion, can be provided on the supporting portion. The hand sensing module is preferably a capacitive sensor, a pressure sensor, an infrared sensor, a sensing electrode plate, or a button switch. After the human finger or the wrist or the arm is placed on the supporting portion, the hand sensing module senses the human finger or the wrist or the arm and then notifies the controller to control the driving device to drive the clamping portion to move relative to the supporting portion and form a closed or opened ring surrounding the human finger or wrist or arm.

In order to facilitate the user to put a finger or a wrist or an arm into the airbag clamp, the body includes main body 10 and armrest 11 provided on main body 10. Supporting portion 450 on airbag clamp 45 is provided on armrest 11. When implementing the present invention, according to the blood pressure detection method is selected based on the actual condition, the size of the human finger or wrist or arm is fit by controlling the size of the airbag clamp.

For symmetry and considerations of maintaining the stiffness and strength, clamping portion 451 comprises first clamping portion 4511 and second clamping portion 4512. Free ends 4513 and driving ends 4514 are respectively provided on first clamping portion 4511 and second clamping portion 4512. Driving ends 4514 of first clamping portion 4511 and second clamping portion 4512 are connected to driving device 452. Free ends 4513 of first clamping portion 4511 and second clamping portion 4512 are moved close to or away from each other when first clamping portion 4511 and second clamping portion 4512 are driven to move relative to the supporting portion by driving device 452, so that detection inlet 454 is expanded or contracted. A detection inlet is formed between the free ends of first clamping portion 4511 and second clamping portion 4512. When the free ends of first clamping portion 4511 and second clamping portion 4512 move close to each other, the detection inlet is narrowed or even closed; and when the free ends of first clamping portion 4511 and second clamping portion 4512 move away from each other, the detection inlet is opened or expanded.

Detection airbag 42 includes airbag body 420 and connecting portions 421 located at two ends of airbag body 420, wherein connecting portions 421 are connected to free ends 4513 of first clamping portion 4511 and second clamping portion 4512. The two ends of detection airbag 42 are respectively connected to free ends 4513 of first clamping portion 4511 and second clamping portion 4512. When the human finger, wrist, or arm is placed in the detection ring, and free ends 4513 of first clamping portion 4511 and second clamping portion 4512 move close to each other, the detection airbag is pulled open and covers the human finger, wrist, or arm.

For fitting the shape of the human finger or wrist or arm to improve the comfort in blood pressure detection, first clamping portion 4511 and second clamping portion 4512 are arc-shaped. Supporting portion 450 includes supporting portion body 4500; wherein supporting portion body 4500 is U-shaped and works as detection ring 453.

In order to maintain a certain strength and stiffness of the clamping portion during blood pressure detection, free end 4513 of first clamping portion 4511 is provided with a protrusion, and free end 4513 of second clamping portion 4512 is provided with a groove fitted with the protrusion provided on free end 4513 of first clamping portion 4511. After free ends 4513 of first clamping portion 4511 and second clamping portion 4512 move close to each other, the above-mentioned protrusions and grooves cooperate with each other, so that first clamping portion 4511, second clamping portion 4512 and the supporting portion together form a stable closed ring. When inflating the detection airbag, the strength and stiffness of the airbag clamp can also be ensured, so as to ensure the accuracy of blood pressure detection results.

Sliding grooves 4501 are provided on supporting portion 450, and first clamping portion 4511 and second clamping portion 4512 are provided with sliding portions 4515 engaged with sliding grooves 4501. Driving device 452 includes first driving rod 4521 and second driving rod 4522, respectively hinged with driving ends 4514 of first clamping portion 4511 and second clamping portion 4512. Driving device 452 further includes movable driving blocks 4523 hinged with the other ends of first driving rod 4521 and second driving rod 4522, driving airbag 4524 provided between movable driving block 4523 and supporting portion 450 and used to push movable driving block 4523 to move, an air pump electrically connected to the controller and used for inflating driving airbag 4524, a solenoid valve or a proportional valve or an exhaust valve electrically connected to the controller for deflating driving airbag 4524, a reset spring provided between supporting portion 450 and movable driving block 4523 and used to push movable driving block 4523 to reset. The movable driving block is located between the driving airbag and the reset spring. The solenoid valve, the proportional valve, or the exhaust valve may also be replaced with other devices that can exhaust the driving airbag. Such replacement is a replacement of conventional technical means and should fall within the protection scope of the present invention.

When the user places a finger or wrist or arm in detection ring 453 through detection inlet 454, the controller controls the air pump to inflate driving airbag 4524 based on the received signal. The signal may be from a key input module or an additionally provided hand sensing module for sensing whether the hand is in the detection ring. The volume of the driving airbag becomes larger and drives the movable driving block to move. The movable driving block pushes first driving rod 4521 and second driving rod 4522 to move. First driving rod 4521 and second driving rod 4522 respectively pushes first clamping portion 4511 and second clamping portion 4512 to slide in the sliding grooves of the supporting portion, so that the free ends of first clamping portion 4511 and second clamping portion 4512 move close to each other, therefore detection inlet 454 is closed or narrowed. The closed or narrowed detection inlet limits the leaving of the human finger, wrist, or arm, so that the controller can control the human blood pressure detection module to start the blood pressure detection. When the blood pressure detection is completed, the controller controls the solenoid valve, the proportional valve, or the exhaust valve to deflate the driving airbag, and the movable driving block is reset by the reset spring and drives the driving rods and first clamping portion 4511 and second clamping portion 4512 to reset at the same time. Detection inlet 454 is opened or expanded again, so that the human finger, the wrist, or the arm can leave from detection ring 453. The power source of the driving device in this embodiment is an air pump, which adopts the pneumatic driving mode. Since the gas is easy to be compressed, the airbag clamp will not cause any big harm to the user even if a pinching phenomenon occurs, which has an advantage of safety.

Airbag clamp 45 further comprises a hand sensing module electrically connected to the controller, wherein the hand sensing module is used to detect whether the human finger, the wrist, or the arm is located in detection ring 453 or on supporting portion 450. When the user places a finger or wrist or arm in detection ring 453 or on supporting portion 450, the hand sensing module informs the controller that the user has sat down, and the controller controls the driving device to drive the clamping portion to move relative to the supporting portion, so that the detection inlet is narrowed or even closed. The controller may further activate the blood pressure detection module to detect the blood pressure. The detection airbag is inflated or deflated and is pressed tightly on the human finger, wrist, or arm. The pressure signal of the blood vessel with respect to the detection airbag is converted into electrical signals by the pressure sensor on the detection airbag, and the electrical signals are transmitted to the controller, and the controller processes the electrical signals to obtain the human blood pressure value and outputs the human blood pressure value through a display or voice prompt module. Of course, it can also be set that the start of human blood pressure detection module needs entering the confirmation from the key input module.

Preferably, the hand sensing module comprises a capacitive sensor or a pressure sensor or a light touch switch or a sensing electrode plate or a button switch or an infrared sensor provided on supporting portion 450 or clamping portion 451 or detection airbag 42, wherein the capacitive sensor or the pressure sensor or the light touch switch or the sensing electrode plate or the button switch or the infrared sensor is electrically connected to controller 3. When a user puts a human finger, a wrist, or an arm in the detection ring, the user directly or indirectly contacts the sensor or the switch. If the capacitive sensor is used, the capacitance of the capacitive sensor is changed, so that the current and voltage of the branch where the capacitive sensor is located are also changed. The controller can identify changes in the current and voltage, so as to control the driving device to narrow the detection inlet. The capacitive sensor can also be replaced by a sensing electrode plate. When a human finger or a wrist or an arm is placed in the detection ring, it contacts the sensing electrode plate, a current branch is formed by the human body and the sensing electrode plate to take away or input a part of the current, and the controller can detect the changes of the current and voltage of the sensing electrode plate and know that the human finger, the wrist, or the arm has entered into the detection ring or on the supporting portion. Of course, the capacitive sensor can also be replaced by a touch switch or an infrared sensor or a pressure sensor. The principle is that the current and voltage of the sensor or the switch of the branch connected to the controller changes, so that the information whether the human body is in the detection position is informed to the controller in form of the electrical signals.

The Embodiment 1 and Embodiment 2 both can be further optimized and improved as below:

In order to facilitate replacement, cleaning and sitting down of the user, body 1 comprises main body 10 and toilet seat 12 pivotally connected to main body 10, wherein after being rotated, toilet seat 12 covers toilet base 2. Main body 10 can also be used as a backrest to make user more comfortable when sitting on toilet base 2. In addition, in order to facilitate operations of the present invention, display or voice prompt module 5 and key input module 6 may be provided on armrest 11.

For smart control, the smart toilet further comprises human body sensing module 7 electrically connected to controller 3 and used for detecting whether the human body has sat down. Wherein "sit down" means that the user sits on toilet base 2 or toilet seat 12.

Human body sensing module 7 comprises a capacitive sensor or a pressure sensor or a sensing electrode plate, wherein the capacitive sensor or the pressure sensor or the sensing electrode plate is electrically connected to controller 3 and used for detecting whether the human body has sat down, and the capacitive sensor or the pressure sensor or the sensing electrode plate are provided on toilet base 2 or body 1. When the person sits down, the capacitive sensor or the pressure sensor or the sensing electrode plate directly or indirectly contacts human body, causing the capacitance of the capacitive sensor to be changed or causing the pressure sensor to generate a piezoelectric effect or causing the current and voltage changes of the circuit connected to the sensor or sensing electrode plate. The changes of the electrical parameters, or the electrical signals, or current and voltage can be recognized by the controller, so that the controller can determine whether the user has sat down.

The human body sensing module uses a capacitive sensor, a pressure sensor, or a sensing electrode plate to sense whether the human body has sat down or not. Of course, the human body sensing module may also sense whether the human body has sat down by the following methods. An infrared detection sensor is used to detect the infrared rays sent from the human body, to sense whether the human body has sat down; the properties of the human bio-electricity or human body conduction are utilized to detect whether the human body has sat down. All the above situations belong to the category of human body sensing detection module and should fall within the protection scope of the present invention.

In order to enrich the functions, the smart toilet further comprises toilet seat temperature controlling module 8 electrically connected to the controller 3 and used for controlling the temperature of the toilet seat, wherein toilet seat temperature controlling module 8 comprises a temperature sensor and a toilet seat heating module which are arranged on the toilet seat and respectively electrically connected to the controller. The toilet seat heating module can include an electric heating tube or electric heating wire or electromagnetic heating group, and further includes some necessary power and control circuits. The user can easily adjust the temperature of the toilet seat through toilet seat temperature control module 8, which is beneficial for enhancing the user experience of the present invention.

The user can set the temperature of the toilet seat through the controller and the key input module. When the temperature sensor detects that the temperature of the toilet seat does not reach the predetermined temperature, the controller controls the toilet seat heating module to heat the toilet seat. When the temperature sensor detects that the temperature of the toilet seat exceeds the predetermined temperature, the controller controls the heating module of the toilet seat to stop heating. The temperature of the toilet seat is stabilized by the above operations at the set temperature.

In order to enrich the functions, the smart toilet further comprises user cleaning module 9 electrically connected to controller 3, and user cleaning module 9 includes water spraying module 90 for providing cleaning water, water pressure control module 91 for controlling the water pressure of the cleaning water, water temperature control module 92 for controlling the water temperature of the cleaning water, fan module 94 for providing drying air and air temperature control module 93 for controlling the temperature of the drying air. Water pressure control module 91, water temperature control module 92, and air temperature control module 93 are electrically connected to controller 3. After using the toilet, the controller is notified by the key input module to start user cleaning module 9, and the user cleaning module cleans and dries the user according to the water temperature, the water pressure and the drying air temperature set by the user. The cleaning includes the hip cleaning and the female cleaning. The cleaning water is provided by the water spraying module. The water spraying module is controlled by the water temperature control module and the water pressure control module. Users can set the water pressure and the cleaning water temperature through the controller. The drying air is provided by the fan module, which is controlled by the air temperature control module, and the user can set the temperature of the drying air through the controller.

The spray module 90 includes a nozzle and a water pipe connecting the nozzle to external water source. The water temperature control module 92 includes the temperature sensor and the cleaning water heating module that are provided on the water pipe and are electrically connected to controller 3 respectively. The water pressure control module 91 includes a proportional valve which is provided between the nozzle and the water pipe and is electrically connected to the controller. The air temperature control module includes a temperature sensor and a drying air heating module that are electrically connected to the controller respectively. The user can set the water temperature and the water pressure of the outlet water of the cleaning water through the controller and the key input module. The controller heats up the cleaning water in the water pipe based on the set water temperature of the cleaning water. The temperature sensor senses the temperature of the cleaning water in the water pipe. If the temperature is lower than the set temperature, cleaning water heating module is started to heat up the cleaning water. If the temperature is higher than the set temperature, the cleaning water heating module is turned off. Thus, the temperature of the outlet water of the cleaning water is kept constant. A proportional valve is provided between the nozzle and the water pipe. The proportional valve is electrically connected to the controller and is controlled by the controller. The controller adjusts an opening degree of the proportional valve based on the set water pressure of the outlet water of the cleaning water, so as to adjust the water pressure of the outlet water of the cleaning water. In addition, the user can also set the temperature of the drying air through the controller. The air temperature control module includes the temperature sensor and the drying air heating module that are electrically connected to the controller respectively. When the temperature of the drying air is lower than the set temperature of drying air, the drying air heating module is started, so as to heat up the drying air. When the temperature of drying air is higher than the set temperature, the heating of drying air is stopped. With the above method, the air temperature control module keeps the temperature of drying air at the set temperature. The drying air heating module and cleaning water heating module can be heating wire, heating rod, electromagnetic heating group, along with corresponding power supply circuit and control circuit.

The smart toilet further includes communication module 31 which is electrically connected to the controller. The communication module 31 communicates with a smart device. The blood pressure value of the human body is transferred through communication module 31 to the smart apparatus and is displayed thereon. The smart apparatus can be a cellphone, a computer, and so on. The communication module communicates with the smart apparatus. The communicating methods can be WIFI, infrared communication, NFC near field communication, and so on. The smart apparatus such as the cellphone can display the blood pressure value of the human body with an APP. Certainly, the smart apparatus can also control the present invention through the communication module.

Figure 7:
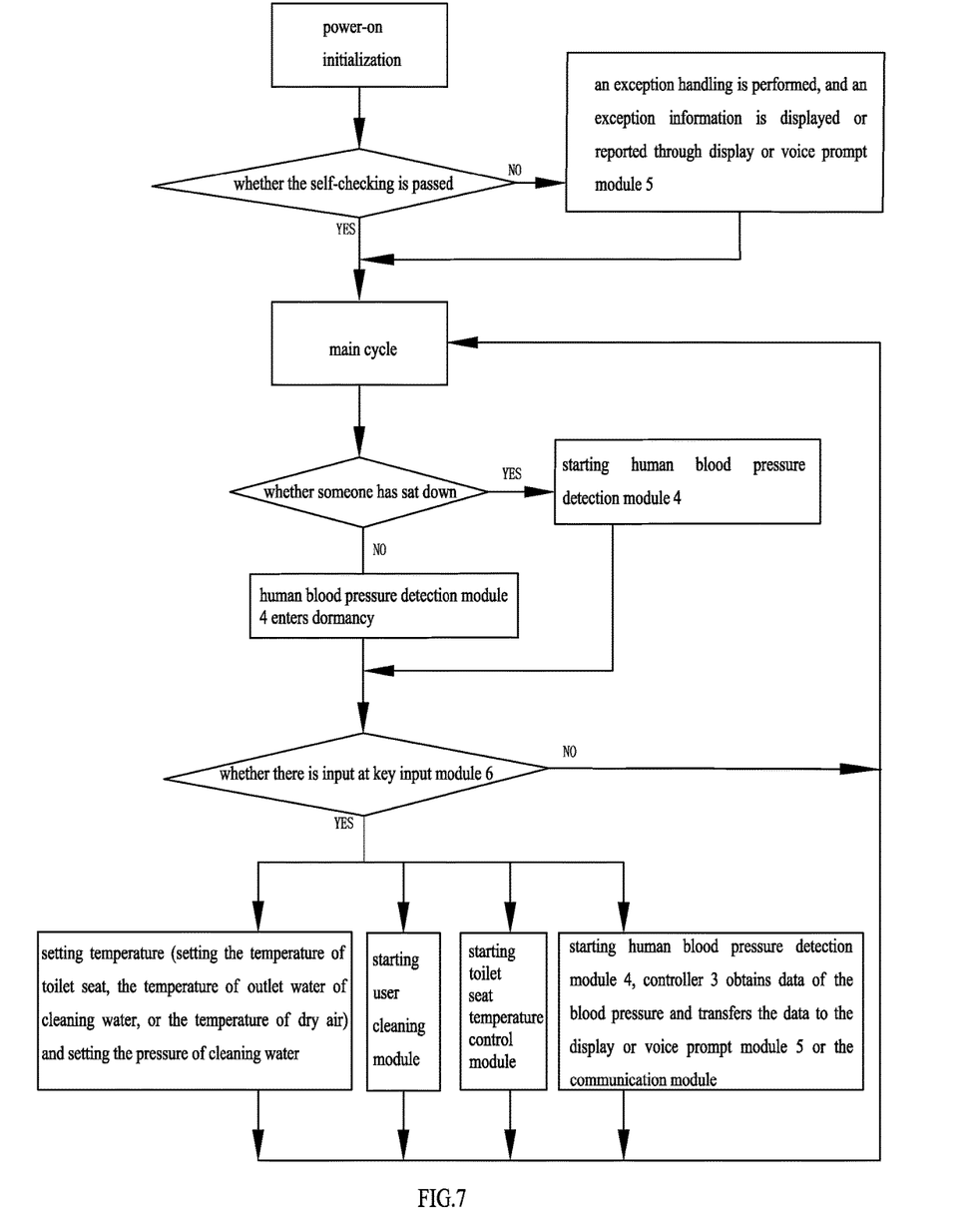
FIG. 7 is a flowchart of a control method of the present invention.

To conveniently control the present invention, a method for controlling the present invention is provided as below:

A control method of a smart toilet with a function of detecting the blood pressure, wherein the method includes the following steps:

A: Power-on and initialization: an initial state of each connected module is initialized through controller 3.

B: Execution of power-on self-checking: fault detection is conducted by controller 3 on each module. If the self-checking is passed, the procedure proceeds to step C. Otherwise, an exception handling is performed, and exception information is displayed or reported through display or voice prompt module 5. The fault detection includes detecting the circuit of each module and the controller circuit for short circuit, disconnection, or current/voltage overload.

C: Entering a main cycle, controller 3 detects whether someone has sat down through human body sensing module 7. If someone has sat down, controller 3 wakes up human blood pressure detection module 4 and performs step D. If no one has sat down, controller 3 controls human blood pressure detection module 4 to enter into dormancy and performs step D. Waking up human blood pressure detection module means that providing power to the human blood pressure detection module, without starting the air pump and the solenoid valve or the proportional valve or the exhaust valve. The dormancy means that cutting off the power provided to the human blood pressure detection module.

D: Controller 3 detects whether there is an input at key input module 6. If there is no input, the procedure returns to step C. If there is an input, the procedure proceeds to step E.

E: Controller 3 performs corresponding operations based on the input at key input module 6, for example, setting the temperature of the cleaning water, the water pressure of the outlet water of the cleaning water, and the temperature of drying air; starting user cleaning module 9 to provide the cleaning water or the drying air.

The smart toilet includes toilet base 2. The smart toilet further includes body 1 which is connected to the toilet base. The body 1 is provided with controller 3 and following modules that are electrically connected to controller 3 respectively, i.e., human blood pressure detection module 4, display or voice prompt module 5, key input module 6 which is used to send the operating information of the user back to the controller 3, and power supply module 30 which is used to provide power. Human blood pressure detection module 4 comprises ring-shaped detection airbag 42 which is closed or non-closed after being inflated when detecting the blood pressure, pressure sensor 41 provided on detection airbag 42 and electrically connected to the controller, air pump 44 configured for inflating detection airbag 42 and solenoid valve or proportional valve or exhaust valve 43 for deflating detection airbag 42, wherein the air pump 44 and solenoid valve or proportional valve or exhaust valve 43 are electrically connected to controller 3 respectively. Human blood pressure detection module 4 further comprises airbag clamp 45 configured to clamp inflated detection airbag 42 on the finger, wrist, or arm of the human body. Controller 3 is used to control air pump 44 and solenoid valve or proportional valve or exhaust valve 43 to inflate or deflate detection airbag 42. Controller 3 processes the electrical signals transmitted by the pressure sensor to obtain the blood pressure value of the human body and controls display or voice prompt module 5 to output the blood pressure value.

The smart toilet further includes human body sensing module 7 which is electrically connected to the controller 3 and is used to sense whether the human body has sat down.

The smart toilet further includes user cleaning module 9 which is electrically connected to controller 3. The user cleaning module 9 includes spray module 90 which provides cleaning water, water pressure control module 91 which controls the pressure of the cleaning water, water temperature control module 92 which controls the temperature of the cleaning water, fan module 94 which provides the drying air, and air temperature control module 93 which controls the temperature of drying air. The water pressure control module 91, water temperature control module 92, and air temperature control module 93 are electrically connected to controller 3.

The body 1 includes main body 10, and toilet seat 12 which is pivotally connected to main body 10, wherein after being rotated, toilet seat 12 covers toilet base 2. The smart toilet further includes the toilet seat temperature control module 8 which is electrically connected to controller 3 and controls the temperature of the toilet seat. The toilet seat temperature control module 8 includes a temperature sensor and a toilet seat heating module that are provided on the toilet seat and are electrically connected to the controller respectively. Step E further includes performing corresponding operations based on the input at key input module 6, for example, setting the temperature of the toilet seat, and starting the toilet seat temperature control module to adjust the temperature of the toilet seat.

Step E further includes performing corresponding operations based on the input at key input module 6. More specifically, controller 3 starts human blood pressure detection module 4. Human blood pressure detection module 4 obtains the electrical signals which are related to the blood pressure and transfers the electrical signals to the controller. The controller processes the obtained electrical signals to obtain the blood pressure value of the human body and controls the display or voice prompt module or communicate module 31 which communicates with the smart device to output the blood pressure value. The starting of the human blood pressure detection module means that the controller controls the air pump, the solenoid valve, the proportional valve, or the exhaust valve, so that the detection airbag is inflated or deflated. The controller processes the electrical signals transmitted from the pressure sensor to obtain the human blood pressure value and controls the display or voice prompt module to output the blood pressure value. Of course, the blood pressure detection module is started by notifying the controller to start up through the key input module after the user puts a finger, wrist, or arm into the airbag clamp. In addition, the airbag clamp can be provided with a hand sensing module electrically connected to the controller and used for sensing whether the hand is in the clamping position of the airbag clamp, so that the hand sensing module can directly notify the controller to start the human blood pressure detection module to detect blood pressure after the hand of the human body is in place.

The human body sensing module 7 includes a capacitive sensor, a pressure sensor, or an inductive electrode plate which is electrically connected to controller 3 and is used to sense whether the user has sat down. The capacitive sensor, the pressure sensor, or the inductive electrode plate is provided on the toilet base 2 or body 1. After the person sits down, the person directly or indirectly contacts the capacitive sensor, the pressure sensor, or the inductive electrode plate, causing the capacitance change of the capacitive sensor, making the pressure sensor generate the piezoelectric effects, or leading to the current change or voltage change of the circuit connected to the sensor or inductive electrode plate. The electrical parameters, the electrical signals, or changes of the current and voltage can be identified by the controller. Therefore, the controller can determine whether the user has sat down. The term "sit down" refers to that the user sits down on the toilet base or the toilet seat.

What is claimed is:

1. A smart toilet with a function of human blood pressure detection, the smart toilet comprising:
   a toilet base,
   a body connected to the toilet base, wherein the body is provided with a controller and a human blood pressure detection module,
   a display or voice prompt module,
   a key input module configured for sending operation information of a user back to the controller, and
   a power supply module for supplying power,
   wherein the human blood pressure detection module, the display or voice prompt module, the key input module and the power supply module are electrically connected to the controller respectively;
   wherein the human blood pressure detection module comprises a detection airbag which is a closed or non-closed ring after being inflated when detecting the blood pressure, a pressure sensor provided on the detection airbag and electrically connected to the controller, an air pump configured for inflating the detection airbag and a solenoid valve or a proportional valve or an exhaust valve for deflating the detection airbag, wherein the air pump and the solenoid valve or the proportional valve or the exhaust valve are electrically connected to the controller respectively;
   wherein the human blood pressure detection module further comprises an airbag clamp provided on the body and configured to clamp the inflated detection airbag on a finger, a wrist, or an arm of a human body; the controller controls the air pump or the solenoid valve or the proportional valve or the exhaust valve to inflate or deflate the detection airbag; the controller processes an electrical signal transmitted by the pressure sensor to obtain a blood pressure value of the human body and controls the display or voice prompt module to output the blood pressure value.

2. The smart toilet with the function of human blood pressure detection according to claim 1, wherein the body comprises a main body and a toilet seat pivotally connected to the main body, wherein after being rotated, the toilet seat covers the toilet base.

3. The smart toilet with the function of human blood pressure detection according to claim 2, wherein the smart toilet further comprises a toilet seat temperature controlling module electrically connected to the controller and used for controlling a temperature of the toilet base, wherein the toilet seat temperature controlling module comprises a temperature sensor and a toilet seat heating module which are arranged on the toilet base and are respectively electrically connected to the controller.

4. The smart toilet with the function of human blood pressure detection according to claim 2, wherein the smart toilet further comprises a human body sensing module electrically connected to the controller and used for detecting whether the human body has sat down.

5. The smart toilet with the function of human blood pressure detection according to claim 1, wherein the body includes a main body and an armrest provided on the main body; the airbag clamp is a finger hole configured on the armrest for inserting the finger; the detection airbag is provided inside the finger hole.

6. The smart toilet with the function of human blood pressure detection according to claim 1, wherein the airbag clamp includes a supporting portion provided on the body and a clamping portion provided on the supporting portion; wherein the supporting portion, the clamping portion, or the supporting portion and the clamping portion is/are provided with or formed with a detection ring for accommodating the human finger or the wrist or the arm; wherein the detection ring is provided with a detection inlet for allowing or restricting the human finger or the wrist or the arm to enter into or leave from the detection ring; wherein the detection airbag is provided on the detection ring;
   the airbag clamp further includes a driving device, wherein the driving device is electrically connected to the controller, and drives the clamping portion to move relative to the supporting portion, such that the detection inlet is expanded or narrowed to allow the human finger or the wrist or the arm to enter into or leave from the detection ring.

7. The smart toilet with the function of human blood pressure detection according to claim 6, wherein the body comprises a main body and an armrest provided on the main body; the supporting portion on the airbag clamp is provided on the armrest.

8. The smart toilet with the function of human blood pressure detection according to claim 6, wherein the clamping portion comprises a first clamping portion and a second clamping portion; a free end and a driving end are respectively provided on each of the first clamping portion and the second clamping portion, driving ends of the first clamping portion and the second clamping portion are connected to the driving device; free ends of the first clamping portion and the second clamping portion move close or away from each other when the first clamping portion and the second clamping portion are driven by the driving device to move relative to the supporting portion, so that the detection inlet is expanded or narrowed.

9. The smart toilet with the function of human blood pressure detection according to claim 8, wherein the detection airbag includes an airbag body and connecting ends located at two ends of the airbag body; wherein the connecting ends are connected to the free ends of the first clamping portion and the second clamping portion.

10. The smart toilet with the function of human blood pressure detection according to claim 8, wherein the first clamping portion and the second clamping portion are arc-shaped; the supporting portion includes a supporting portion body; wherein the supporting portion body is U-shaped and works as the detection ring.

11. The smart toilet with the function of human blood pressure detection according to claim 8, wherein the free end of the first clamping portion is provided with a protrusion, and the free end of the second clamping portion is provided with a groove fitted with the protrusion provided on the free end of the first clamping portion.

12. The smart toilet with the function of human blood pressure detection according to claim 8, wherein sliding grooves are provided on the supporting portion, the first clamping portion and the second clamping portion are each provided with a sliding portion for engaging with the sliding grooves; the driving device includes a first driving rod and a second driving rod respectively hinged with the driving ends of the first clamping portion and the second clamping portion, a movable driving block hinged with the other ends of the first driving rod and the second driving rod, a driving airbag provided between the movable driving block and the supporting portion to push the movable driving block to move, an air pump electrically connected to the controller and used for inflating the driving airbag, the solenoid valve or the proportional valve or the exhaust valve electrically connected to the controller for deflating the driving airbag, a reset spring provided between the supporting portion and the movable driving block to push the movable driving block to reset; wherein the movable driving block is located between the driving airbag and the reset spring.

13. The smart toilet with the function of human blood pressure detection according to claim 6, wherein the airbag clamp further comprises a hand sensing module electrically connected to the controller; wherein the hand sensing module is used to detect whether the human finger or the wrist or the arm is located in the detection ring or on the supporting portion.

14. The smart toilet with the function of human blood pressure detection according to claim 13, wherein the hand sensing module comprises a capacitive sensor or a pressure sensor or a light touch switch or a sensing electrode plate or a button switch or an infrared sensor provided on the supporting portion or the clamping portion or the detection airbag, wherein the capacitive sensor or the pressure sensor or the light touch switch or the sensing electrode plate or the button switch or the infrared sensor is electrically connected to the controller.

15. The smart toilet with the function of human blood pressure detection according to claim 1, wherein the airbag clamp comprises a supporting portion arranged on the body, a clamping portion arranged on the supporting portion, a driving device electrically connected to the controller; wherein the driving device drives the clamping portion to move relative to the supporting portion, such that the clamping portion, or the supporting portion and the clamping portion form a closed or non-closed ring which surrounds the human finger or the wrist or the arm; wherein the detection airbag is provided on the clamping portion and/or the supporting portion.

16. The smart toilet with the function of human blood pressure detection according to claim 15, wherein that the body comprises a main body and an armrest provided on the main body; the supporting portion on the airbag clamp is provided on the armrest.

17. The smart toilet with the function of human blood pressure detection according to claim 15, wherein the airbag clamp further comprises a hand sensing module electrically connected to the controller; wherein the hand sensing module is used to detect whether the human finger or the wrist or the arm is located in the detection ring or on the supporting portion.

18. The smart toilet with the function of human blood pressure detection according to claim 1, wherein the smart toilet further comprises a human body sensing module electrically connected to the controller and used for detecting whether the human body has sat down.

19. The smart toilet with the function of human blood pressure detection according to claim 18, wherein the human body sensing module comprises a capacitive sensor or a pressure sensor or a sensing electrode plate, wherein the capacitive sensor or the pressure sensor or the sensing electrode plate is electrically connected to the controller, and used for detecting whether the user has sat down; and the capacitive sensor or the pressure sensor or the sensing electrode plate is provided on the toilet base or the body.

20. The smart toilet with the function of human blood pressure detection according to claim 1, wherein the smart toilet further comprises a user cleaning module electrically connected to the controller, and the user cleaning module includes a water spraying module for providing cleaning water, a water pressure control module for controlling water pressure of the cleaning water, a water temperature control module for controlling a water temperature of the cleaning water, a fan module for providing drying air and an air temperature control module for controlling a temperature of the drying air; wherein the water pressure control module, the water temperature control module, the air temperature control module are electrically connected to the controller.

21. The smart toilet with the function of human blood pressure detection according to claim 20, wherein the water spraying module comprises a water outlet nozzle, a water pipe connected to the water outlet nozzle and the external water source; the water temperature control module comprises a first temperature sensor and a cleaning water heating module which are respectively arranged on the water pipe and electrically connected to the controller; the water pressure control module comprises a proportional valve provided between the water outlet nozzle and the water pipe and electrically connected to the controller; the air temperature control module comprises a second temperature sensor and a drying air heating module respectively electrically connected to the controller.

22. The smart toilet with the function of human blood pressure detection according to claim 1, wherein the smart toilet further comprises a communication module electrically connected to the controller, the communication module communicates with a smart device, wherein the human blood pressure value is transmitted to the smart device and displayed on the smart device by the communication module.

23. A method for controlling a smart toilet with human blood pressure detecting function, comprising the following steps:
step A, initializing an initial state of each connection module through a controller;
step B, performing fault detection on each module through the controller; if self-checking is passed, proceeding to step C; otherwise, conducting an exception handling, displaying or reporting exception information through a display or voice prompt module;
step C, entering into a main cycle, detecting whether a person has sat down by the controller through a human body sensing module; if the person has sat down seats, starting a human blood pressure detection module by the controller and proceeding to step D; if no one has sat down, controlling the human blood pressure detection module, by the controller, to enter dormancy and proceeding to step D;
step D, detecting whether there is an input at a key input module by the controller, if there is no input, returning to the step C; if there is the input, proceeding to step E;

step E, performing corresponding operations by the controller based on the input at the key input module: setting a temperature of cleaning water, a water pressure of the cleaning water, a temperature of drying air, and starting a user cleaning module to provide the cleaning water or the drying air;

wherein the smart toilet comprises a toilet base, and further comprises a body connected to the toilet base, the body is provided with the controller and a human blood pressure detection module, a display or voice prompt module, a key input module configured for sending operation information of a user back to the controller, and a power supply module for supplying power, wherein the human blood pressure detection module, the display or voice prompt module, the key input module and the power supply module are electrically connected to the controller respectively; wherein the human blood pressure detection module comprises a detection airbag which is a closed or non-closed ring after being inflated when detecting the blood pressure, a pressure sensor provided on the detection airbag and electrically connected to the controller, an air pump configured for inflating the detection airbag and a solenoid valve or a proportional valve or an exhaust valve for deflating the detection airbag, wherein the air pump and the solenoid valve or the proportional valve or the exhaust valve are electrically connected to the controller;

wherein the human blood pressure detection module further comprises an airbag clamp provided on the body and configured to clamp an inflated detection airbag on a finger, a wrist, or an arm of the human body; the controller is used to control the air pump or the solenoid valve or the proportional valve or the exhaust valve to inflate or deflate the detection airbag; the controller processes an electrical signal transmitted by the pressure sensor to obtain a blood pressure value of the human body and controls the display or voice prompt module to output the blood pressure value;

wherein the smart toilet further comprises a human body sensing module electrically connected to the controller and used for sensing whether the human body has sat down;

wherein the smart toilet further comprises a user cleaning module electrically connected to the controller, and the user cleaning module includes a water spraying module for providing cleaning water, a water pressure control module for controlling the water pressure of the cleaning water, a water temperature control module for controlling the water temperature of the cleaning water, a fan module for providing drying air and an air temperature control module for controlling the temperature of the drying air; wherein the water pressure control module, the water temperature control module, the air temperature control module are electrically connected to the controller.

24. The method for controlling the smart toilet with human blood pressure detecting function according to claim 23, wherein the body comprises a main body and a toilet seat pivotally connected to the main body, wherein after being rotated, the toilet seat covers the toilet base;

the smart toilet further comprises a toilet seat temperature controlling module electrically connected to the controller and used for controlling the temperature of the toilet base, wherein the toilet seat temperature controlling module comprises a temperature sensor and a toilet seat heating module which are respectively arranged on the toilet base and are respectively electrically connected to the controller; the step E further comprises performing corresponding operations according to the input of the key input module: setting a temperature of the toilet seat, and starting the toilet seat temperature controlling module to adjust the temperature of the toilet seat.

25. The method for controlling an smart toilet with human blood pressure detecting function according to claim 23, wherein the step E further comprises performing corresponding operations according to the input of the key input module:

starting the human blood pressure detection module by the controller, obtaining the electrical signal related to the human blood pressure and transmitting the electrical signal to the controller by the pressure sensor;

processing the obtained electrical signal to obtain the blood pressure value of the human body and controlling the display or voice prompt module or the communication module which communicates with the smart device to output the blood pressure value by the controller.

26. The method for controlling the smart toilet with human blood pressure detecting function according to claim 23, wherein the human body sensing module comprises a capacitive sensor or a pressure sensor or a sensing electrode plate, wherein the capacitive sensor or the pressure sensor or the sensing electrode plate is electrically connected to the controller and used for detecting whether the human body has sat down; and the capacitive sensor or the pressure sensor or the sensing electrode plate is provided on the toilet base or the body.

* * * * *